United States Patent
Baker et al.

(10) Patent No.: US 12,180,524 B2
(45) Date of Patent: Dec. 31, 2024

(54) EPIGENETIC MODIFICATION OF FUNGI AND USES THEREOF

(71) Applicants: University of South Florida, Tampa, FL (US); INSTITUTO POLITÉCNICO NACIONAL, Mexico City (MX); KING ABDULAZIZ UNIVERSITY, Jeddah (SA)

(72) Inventors: Bill J. Baker, Temple Terrace, FL (US); Dennis E. Kyle, Athens, GA (US); Mario Alberto Rodriguez-Pérez, Reynosa (MX); Anne-Claire D. Limon, Tampa, FL (US); Ala Azhari, Tampa, FL (US)

(73) Assignees: UNIVERSITY OF SOUTH FLORIDA, Tampa, FL (US); INSTITUTO POLITÉCNICO NACIONAL, Mexico City (MX); KING ABDULAZIZ UNIVERSITY, Jeddah (SA)

( * ) Notice: Subject to any disclaimer, the term of this patent is extended or adjusted under 35 U.S.C. 154(b) by 427 days.

(21) Appl. No.: 17/406,025

(22) Filed: Aug. 18, 2021

(65) Prior Publication Data

US 2022/0136019 A1 May 5, 2022

Related U.S. Application Data

(63) Continuation of application No. 16/443,278, filed on Jun. 17, 2019, now abandoned.

(60) Provisional application No. 62/764,800, filed on Aug. 16, 2018.

(51) Int. Cl.
| | |
|---|---|
| *A61K 31/366* | (2006.01) |
| *A61P 33/02* | (2006.01) |
| *C12N 1/14* | (2006.01) |
| *C12P 17/18* | (2006.01) |

(52) U.S. Cl.
CPC .......... *C12P 17/181* (2013.01); *A61K 31/366* (2013.01); *A61P 33/02* (2018.01); *C12N 1/14* (2013.01)

(58) Field of Classification Search
CPC .............................. A61K 31/366; A61P 33/02
See application file for complete search history.

(56) References Cited

U.S. PATENT DOCUMENTS

2017/0050946 A1  2/2017 Demers et al.

OTHER PUBLICATIONS

Costa et al., "Diversity of Leaf Endophytic Fungi in Mangrove Plants of Northeast Brazil", Sep. 2012, Brazilian Journal of Microbiology, vol. 43, No. 3, pp. 1165-1173. (Year: 2012).*
Wang et al., "Bioactive Natural Compounds from the Mangrove Endophytic Fungi", Apr. 1, 2014, Mini-Reviews in Medicinal Chemistry, vol. 14, No. 4, pp. 370-391. (Year: 2014).*
Cichewicz, "Epigenome manipulation as a pathway to new natural product scaffolds and their congeners", 2010, Natural Product Reports, vol. 27, pp. 11-22. (Year: 2010).*
Chaturvedula et al., "New Cytotoxic Lupane Triterpenoids from the Twigs of Coussarea paniculata", Feb. 7, 2003, Journal of Natural Products, vol. 66, Issue 3, pp. 419-422. (Year: 2003).*
Mukhtar et al., "A New d-Lactone Containing Triterpene from the Flowers of Calendula officinalis", 2004, Pharmaceutical Biology, vol. 42, Nos. 4-5, pp. 305-307. (Year: 2004).*
ACD Limon, et al. "Isolation of metabolites from epigenetically modified mangrove fungi for anti-infective drug discovery" Congress Abstract, Planta Med 2016; 82(S 01): s1-S381.
Ancheeva, et al. "Lead Compounds from Mangrove-Associated Microoganisms." Mar. Drugs, 2018, 16:319.
Azhari, et al. "Identification of Novel Hits Against." (2018). Graduate Theses and Dissertations. http://scholarcommons.usf.edu/edt/7123, pp. 1-194.
Beau, et al. "Epigenetic Tailoring for the Production of Anti-Infective Cytosporones from the Marine Fungus *Leucostoma persoonii*." Mar. Drugs, 2012, 10, 762-774.
Calcul, et al. "Screening Mangrove Endophytic Fungi for Antimalarial Natural Products." Mar. Drugs, 2013, 11, 5036-5050.
Chaturvedula et al. "New Cytotoxic Lupane Triterpenoids from the Twigs of Coussarea paniculata." J. Natural Prod. (2003) 66: 419-422.
Cichewicz "Epigenome manipulation as a pathway to new natural product scaffolds and their congeners." Natural Products Reports (2010) 27: 11-22.
Costa et al. "Diversity of Leaf Endophytic Fungi in Mangrove Plants of Northeast Brazil." Brazilian J. Microbiol (2012): 1165-1173.
Demers, et al. "Exploitation of Mangrove Endophytic Fungi for Infectious Disease Drug Discovery." Mar. Drugs, 2018, 16, 376, pp. 1-11.
Deshmukh, et al. "Mangrove—Associated Fungi: A Novel Source of Potential Anticancer Compounds." J. Fungi, 2018, 4:101.
Imhoff, Johannes. "Natural Products from Marine Fungi—Still an Underrepresented Resource." Mar. Drugs, 2016, 14:19.
Molinski TF, et al. "Metabolites of the Antarctic Sponge Dendrilla membranosa." J. Org. Chem. 1987, 52, 296-298, 1987 American Chemical Society.
Mukhtar et al. "A new ?- LactoneContaning Triterpene from the Flowers of Calendula officinalis." Pharmaceutical Biol. (2004) 42(4-5): 305-307.
Nicoletti, et al. "Secondary Metabolites of Mangrove-Associated Strains of Talaromyces." Mar. Drugs, 2018, 16:12.

(Continued)

Primary Examiner — Michael B. Pallay
(74) Attorney, Agent, or Firm — Quarles & Brady LLP

(57) ABSTRACT

Described herein are methods of epigenetic modification of fungi and uses thereof. Also described herein are compounds that can have antileishmanial activity and formulations thereof. Also described herein are methods of treating leishmanial infection in a subject that include the step of administering a compound or formulation thereof described herein to the subject.

5 Claims, 19 Drawing Sheets

(56) References Cited

OTHER PUBLICATIONS

S Soldatou, et al. "Isolation of bioactive secondary metabolites from mangrove fungal endophytes using epigenetic regulation." Congress Abstract, Planta Med 2016; 82(S01): S1-S381.

Sal Thomas et al. "Isolation of bioactive secondary metabolites from mangrove fungal endophytes using epigenetic regulation", Congress Abstract, Planta Med 2016; 82(S 01): S1-S381.

Tuan Noraida Tuan Hamzah et al. "Diversity and Characterization of Endophytic Fungi Isolated From the Tropical Mangrove Species, *Rhizophora mucronata*, and Identification of Potential Antagonists Against the Soil-Borne Fungus, *Fusarium solani*." Jul. 2018 | vol. 9 | Article 1707, Frontiers in Microbiology www.frontiersin.org pp. 1-17.

Wang, et al. "Advances in the Study of Structures and Bioactivites of Metabolites Isolated from Mangrove-Derived Fungi in the South China Sea." Mar. Drugs, 2013, 11:3601-3616.

Wang et al. "Bioactive Natural Compounds from the Mangrove Endophytic Fungi." Med. Chem. (2014) 14: 370-391.

Wang, et al. "Sharing and community curation of mass spectrometry data with GNPS." Nat Biotechnol. Author manuscript; available in PMC Feb. 2, 20173., pp. 1-34.

Zhang, et al. "Polyketides from the Mangrove-Derived Endophytic Fungus *Cladosporium cladosporioides*." Mar. Drugs, 2019, 17:296.

\* cited by examiner

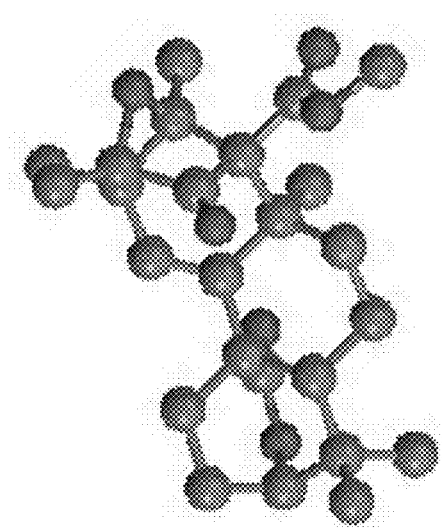
ACDL-34
1.2 mg
Cytotox.: >50 μg/mL
IM IC 50: 0.61 μg/mL
Selectivity Index: 29
FIG. 4A
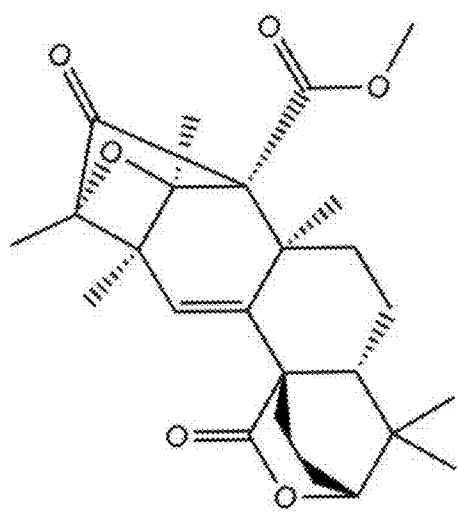

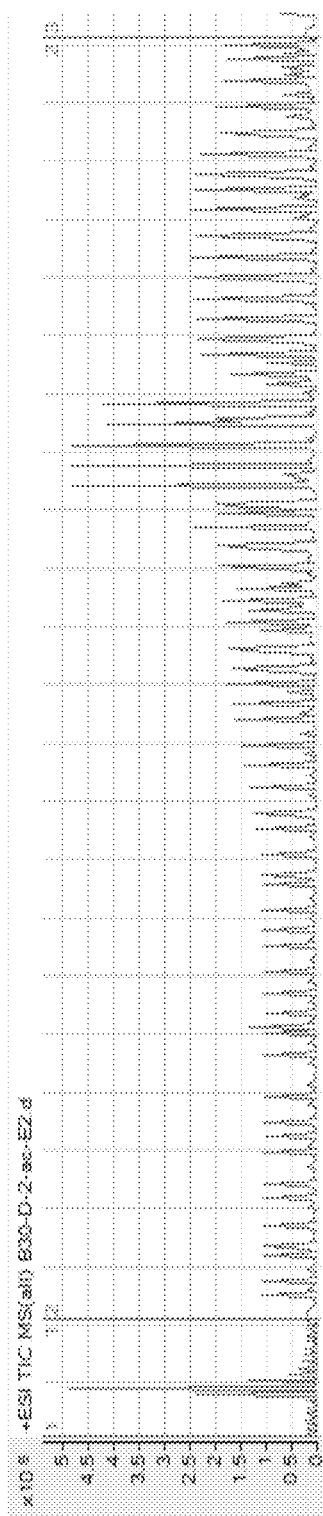
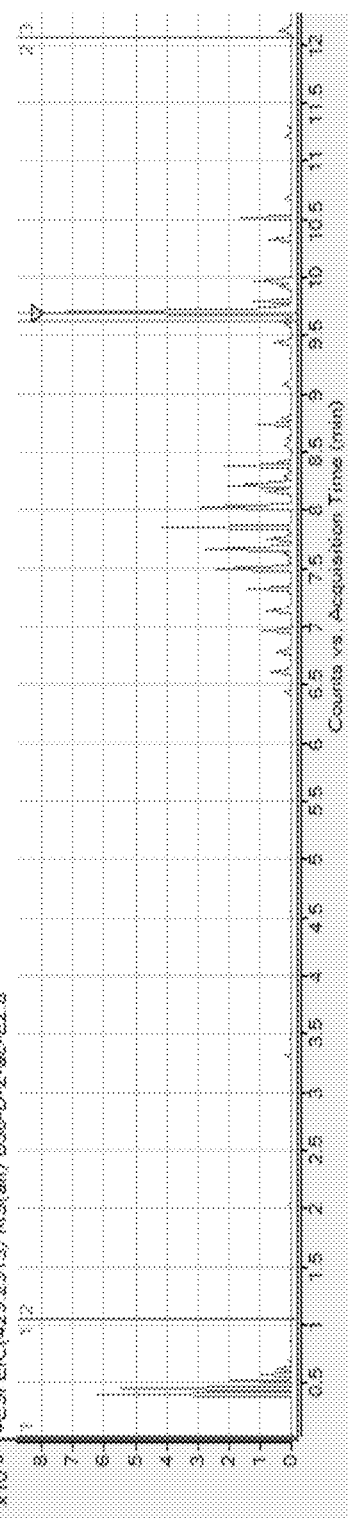
FIG. 10A
FIG. 10B
FIG. 10C

EPIGENETIC MODIFICATION OF FUNGI AND USES THEREOF

CROSS-REFERENCE TO RELATED APPLICATIONS

This application is a continuation of U.S. application Ser. No. 16/443,278, filed Jun. 17, 2019, which claims priority to U.S. Provisional Application entitled "EPIGENETIC MODIFICATION OF FUNGI AND USES THEREOF," having Ser. No. 62/764,800, filed on Aug. 16, 2018. The entire content of each of the above-referenced applications is incorporated herein by reference.

STATEMENT REGARDING FEDERALLY SPONSORED RESEARCH

This invention was made with government support under AI103673 awarded by the National Institutes of Health. The Government has certain rights in the invention.

BACKGROUND

Pathogen resistance, appearance of new disease, and lack of effective treatments and/or preventatives for neglected diseases are significant problems worldwide. As such, there exists a need for the development of disease treatments and/or preventatives.

SUMMARY

Described herein are methods of producing compounds in a fungus. Methods as described herein can comprise culturing a population of fungal cells in vitro; exposing the population of fungal cells to an epigenetic modulator; and extracting compounds from the population of fungal cells to obtain extracted compounds.

The culturing can be performed with a media. In embodiments according to the present disclosure, the media is selected from the group consisting of: rice, action agar glycerol, potato dextrose and agar, Sabaurough dextrose broth and agar, and malt broth and agar.

The culturing can be performed at a temperature. In embodiments according to the present disclosure, the temperature can be 23° C. or 30° C.

The culturing can be performed in light or dark.

The culturing can be performed with an amount of fungus inoculated. In embodiments according to the present disclosure, the amount of fungus inoculated can be 2 pieces, 4 pieces, or 8 pieces.

The culturing can be performed at acidic or basic pH.

The culturing can be performed at a saline percent. In embodiments according to the present disclosure, the saline percent (i.e. salinity) can be about 0.34% or about 0.68%.

The culturing can be performed for a cultivation period. In embodiments according to the present disclosure, the cultivation period can be 7 days or 14 days, or about 7 days to about 14 days.

In embodiments according to the present disclosure, methods as described herein can further comprise the step of partitioning the extracted compounds to obtain partitioned compounds.

In embodiments according to the present disclosure, methods as described herein can further comprise purifying or otherwise isolating the extracted compounds to obtain purified compounds. In embodiments according to the present disclosure, the purification is carried out using liquid chromatography. In embodiments of the present disclosure, the purified compounds can be concentrated to a higher amount than what is present otherwise.

In embodiments according to the present disclosure, methods as described herein can further comprise performing an activity assay to determine the anti-infective efficacy of the extracted compounds, partitioned compounds, and/or purified compounds.

In embodiments according to the present disclosure, the fungus can be an endophytic fungus. In embodiments according to the present disclosure, the fungus is a mangrove fungus.

In embodiments according to the present disclosure, the epigenetic modifier can be an HDAC inhibitor. In embodiments according to the present disclosure, the HDAC inhibitor is sodium butyrate.

In embodiments according to the present disclosure the epigenetic modifier can be a DNMT inhibitor. In embodiments according to the present disclosure, the DNMT inhibitor is 5-azacytidine.

Also described herein are compositions. Compositions as described herein can comprise Compound (1):

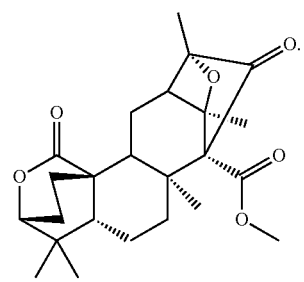

(1)

The composition can be effective to kill and/or inhibit a leishmanial parasite.

Described herein are pharmaceutical formulations. Pharmaceutical formulations can comprise:

an amount of Compound (1)

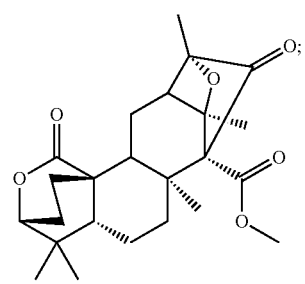

(1)

and a pharmaceutically acceptable carrier.

The amount can be an effective amount sufficient to kill and/or inhibit a leishmanial parasite. In embodiments according to the present disclosure, the amount of Compound (1) can range from about 0.01 µg to about 1000 mg or more. In embodiments according to the present disclosure, the amount of Compound (1) can range from about 0.01 µg to about 1000 mg.

Further described herein are methods of treating leishmanial infection in a subject in need thereof. Methods of treating leishmanial infection in a subject in need thereof can comprise administering an amount of a composition as described herein or a pharmaceutical formulation as described herein to the subject in need thereof.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 2 FIGS. 4A-4C show a structure, cytotoxicity, NMR and other characteristics of a compound produced in epigenetically modified mangrove cells that has anteishmanial efficacy.

FIGS. 8A-8B are results at 23° C. with light (FIG. 8A) and dark (FIG. 8B), and FIGS. 8C-8D are results at 30° C. with light (FIG. 8C) and dark (FIG. 8D).

FIGS. 10A-10C are a continuation of the LC MS MS data of FIGS. 9A-9C for both best cultures found

DETAILED DESCRIPTION

Figure 1:
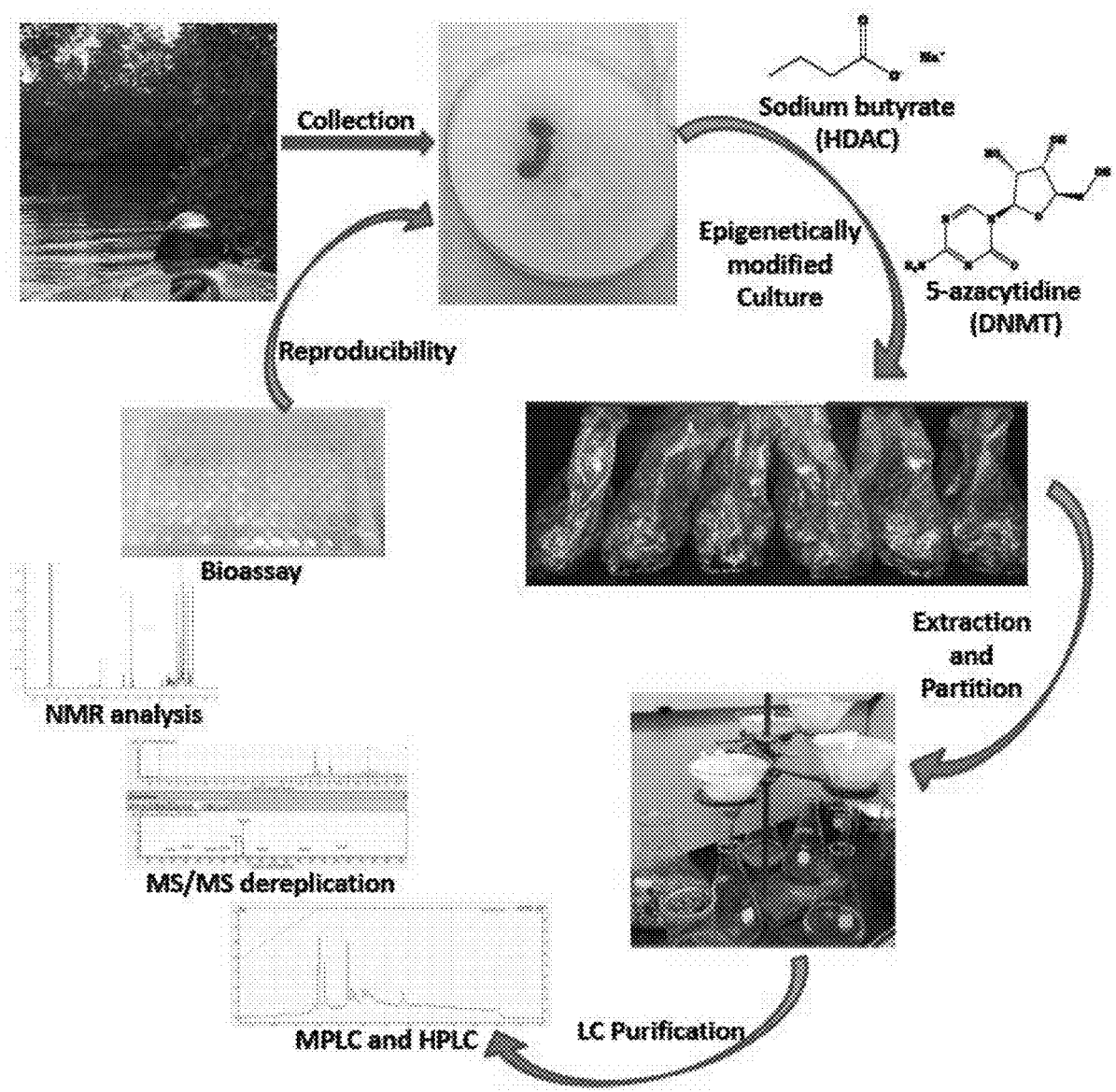
FIG. 1 shows a general schematic of a method to produce and characterize compounds via epigenetic modification of fungal cells in vitro.
Figure 2:
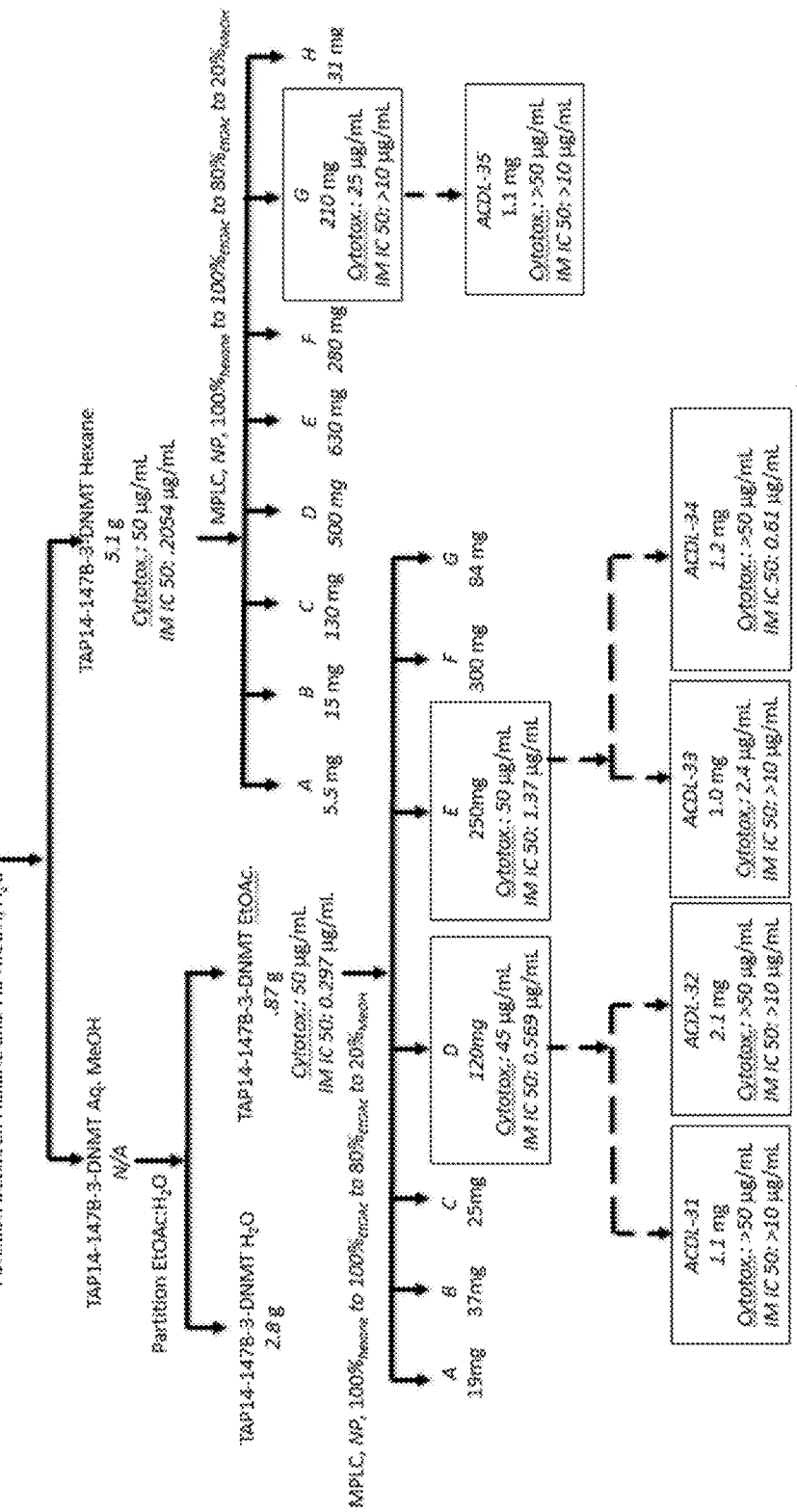
FIG. 2 shows a partitioning scheme to obtain antileishmanial compounds produced in epigenetically modified mangrove fungal cells.
Figure 3A:
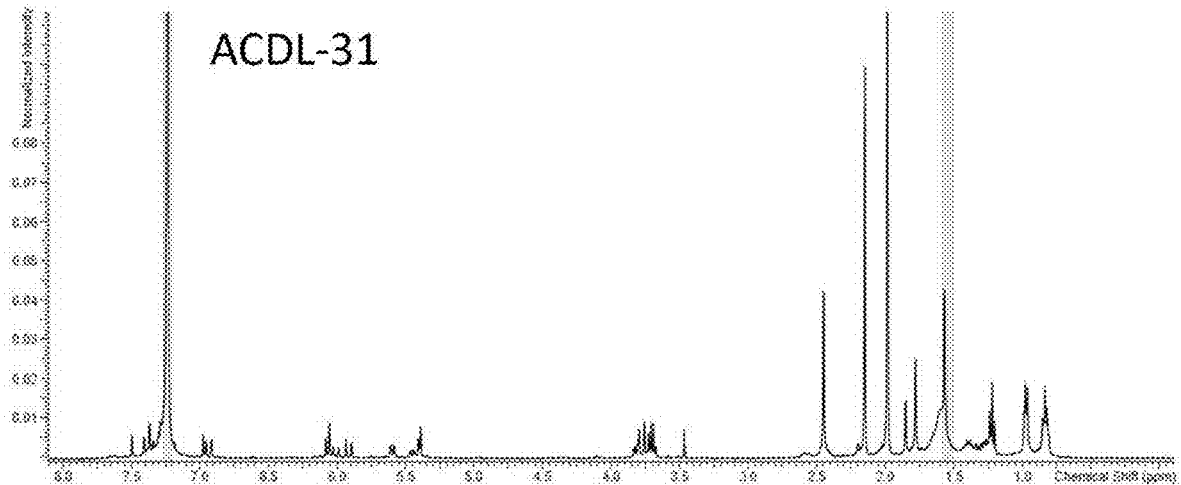
FIGS. 3A-3D shows NMR analysis results from compounds partitioned according to the scheme if
Figure 3B:
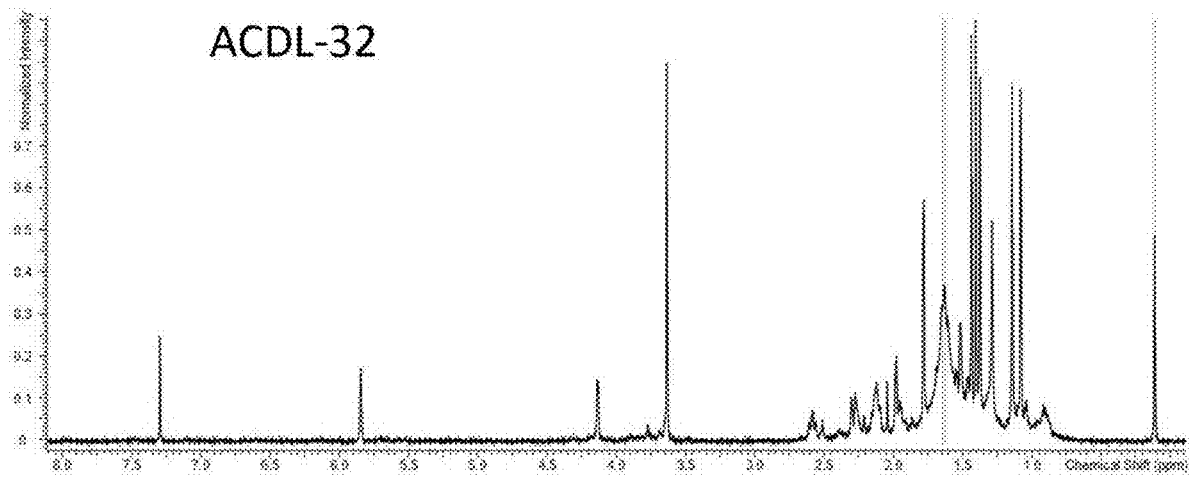
Figure 3C:
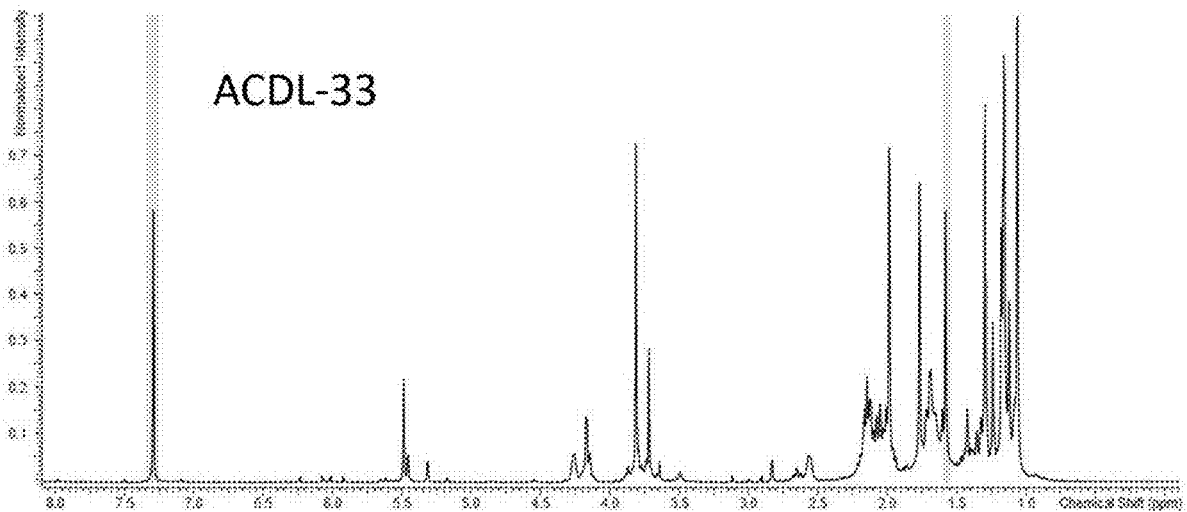
Figure 3D:
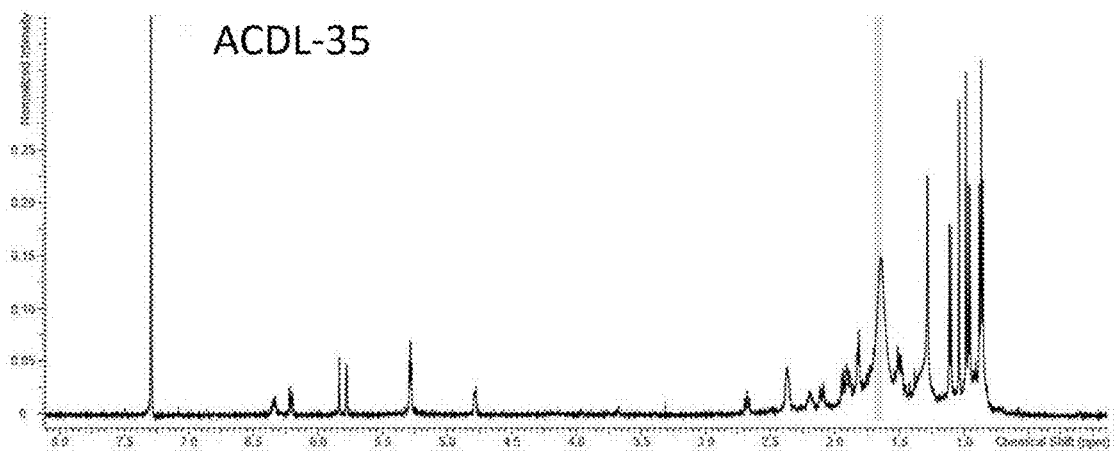

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" Includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Definitions

As used in the specification and the appended claims, the singular forms "a," "an" and "the" include plural referents unless the context clearly dictates otherwise.

As used herein, the terms "optional" or "optionally" means that the subsequently described event or circumstance can or cannot occur, and that the description includes instances where said event or circumstance occurs and instances where it does not.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravitreal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "amphiphilic" refers to a molecule combining hydrophilic and lipophilic (hydrophobic) properties.

As used herein, "attached" refers to a covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used herein, "dose," "unit dose," or "dosage" refers to physically discrete units suitable for use in a subject, each unit containing a predetermined quantity of Compound (1) and/or a formulation thereof calculated to produce the desired response or responses in association with its administration.

As used herein, "effective amount" (or amount effective) refers to the amount of a compound provided herein that is sufficient to effect beneficial or desired biological, emotional, medical, or clinical response of a cell, tissue, system, animal, or human. An effective amount can be administered in one or more administrations, applications, or dosages. The term cam also include within its scope amounts effective to enhance or restore to substantially normal physiological function. The "effective amount" can refer to the amount of the compounds (e.g. a compound (1)) or formulations thereof described herein that can allow for treating a leishmaniosis infection in a subject in need thereof by reducing or eliminating symptoms related to the leishmaniosis infection.

The term "hydrophilic", as used herein, refers to substances that have strongly polar groups that are readily soluble in water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein "peptide" refers to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "Individual," or "patient" refers to a vertebrate organism, such as a mammal (e.g. human). "Subject" can also refer to a cell, a population of cells, a tissue, an organ, or an organism, preferably to human and constituents thereof.

As used herein, "substantially pure" means an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," refers to an amount (e.g. mass, volume, dosage, concentration, and/or time period) needed to achieve one or more desired result(s). For example, a therapeutically effective amount refers to an amount needed to achieve one or more therapeutic effects. In some embodiments, the effective amount can be anti-parasitic. In some embodiments, the effective amount can kill and/or inhibit a leishmanial parasite. In some embodiments, the effective amount can treat a leishmanial infection in a subject.

Discussion

Pathogen resistance, appearance of new disease, and lack of effective treatments and/or preventatives for neglected diseases are significant problems worldwide. In particular, Leishmaniasis is a disease transmitted by the bite of a sandfly. Up to 12 million people are estimated to be infected, a number that increases by 2 million annually. Tens of thousands of deaths result annually from the infection, and countless individuals suffer painful and disfiguring physical manifestations. Current treatments can be costly and/or have toxic side effects. As such, there exists a need for the development of treatments and/or preventatives for leishmaniasis and other diseases.

With that said, described herein methods of generating compounds from fungi that can include the steps of epigenetically modifying a fungi and uses thereof. Also described herein are antileishmanial compounds and methods of treating a leishmaniosis infection in a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Epigenetic Modification of Fungi and Uses Thereof

Described herein are methods of epigenetic modification of fungi and uses thereof. FIG. 1 shows a general process of epigenetically modifying a fungus and the production of one or more compounds. In some aspects, a population of fungal cells can be grown in culture in a suitable fungal growth medium. In culture, the fungal cells can be grown and/or maintained. In some embodiments, the fungal cells can be from an endophytic fungus of a mangrove plant.

The fungus from the mangrove plant can be one or more of the genera *Cladosporium, Talaromyces, Penicillium, Fusarium, Cladosporium, Aspergillus, Trichoderma, Stachybotrys, Halorosellinia, Guignardia, Nigrospora, Alternaria, Paecilomyces, Xylaria, Diaporthe, Pestalodopsis, Phomopsis, Sporothrix, Rhytidhysteron, Lasiodiplodia, Pseudoiagarobasidium, Mucor, Eurotium, Trichoderma, Phoma, Stemphylium, Paradictyoarthrinium, Bionectria, Fusarium, Diaporthe, Acremonium, Sporothrix, Campylocarpon, Dothiorella, Acremonium, Sarocladium, Annulohypoxylon, Nigrospora, Eutypella,* and *Halorosellinia*. Species of these genera are known in the art to the skilled artisan. The fungus can be of the species *Cladosporium cladosporioides*. In an embodiment, the fungus is an endophytic fungus of the La Encrucijada tropical mangrove of Tapachula (Chiapas, Mexico), deposited at the American Type Culture Collection (ATCC) Patent Depository, 10801 University Blvd. Manassas, Virginia, 20110-2209 USA, on Mar. 20, 2024, under accession number PTA-127738, pursuant to the Budapest Treaty on the International Recognition of the Deposit of Microorganisms for the Purposes of Patent Procedure.

The fungal cells can be exposed to an amount of one ore epigenetic modifying agent (also referred to herein as an epigenetic modifier). The epigenetic modifier can result in an increase in methylation and/or acetylation of the chromatin or component thereof (e.g. histone and/or DNA) of the fungal cell(s). Suitable epigenetic modifiers can include, but are not limited to, compounds and compositions thereof that stimulate or inhibit (e.g. modify) DNA methyl transferases (DNMTs), histone demethylases (HDMs), histone acetyl transferase (HATs), histone deacetylases (HDACs), and/or chromatin remodelers. By stimulating or inhibiting DNMTs, HDMs, HATs, and/or HDACs, the epigenetic status can be altered. Epigenetic modifiers can include DMT activators and inhibitor, HDM activators and inhibitors, HAT activators and inhibitors, HDAC activators and inhibitors, and other chromatin remodeler activators and inhibitors. Suitable epigenetic modifiers include, but are not limited to, 5-azacytine, 5-Aza-2'deoxycytidine, 5-Fluoro-2'deoxycytidine, 5,6-Dihdro-5-azacytidine, Zebularine (1-(β-D-ribofuranosyl)-1,2-dihydropyrimidin-2-one), Hydralazine, procainamide, EGCG, RG108, and SGI-110, disulfiram, 1-Hydrazinophthalazine hydrochloride, 5-Azacytidine-15N4, Psammaplin A, SG11027, suberoylanilide hydroxamic acid (SAHA/Vorinostat/Zolinza), Trichostatin A (TSA), PXD-101), cyclic peptides (e.g. FK228/romidespin/ISTODAX®), benzamide derivatives (e.g. entinostat (MS-275) and DMGCD0103), aliphatic acids (e.g. valproic acid and sodium phenylbutyrate), 3-Deazaneplanocin A, UNC0638, BIX01294, AMI1, Sinefungin, PRMT1 inhibitor 6e, C 7280948, AMI-5 (Eosin Y), JIB 04, UNC1999, chaetocin, DOT1L Inhibitor (Compound 55), C-646 (4-[4-[[5-(4,5-Dimethyl-2-nitrophenyl)-2-furanyl]methylene]-4,5-dihydro-3-methyl-5-oxo-1H-pyrazol-1-yl]benzoic acid), CPTH2 (Cyclopentylidene-[4-(4'-chlorophenyl)thiazol-2-yl]hydrazine), CTPB (N-(4-chloro-3-trifluoromethyl-phenyl)-2-ethoxy-6-pentadecyl-benzamide), garcinol, anacardic acid, MG149, SRTCX1003, sodium butyrate, procaine hydrochloride, procaine, lomeguatrib and combinations thereof. Other suitable epigenetic modifiers will be appreciated by one of ordinary skill in the art in view of this description.

Manipulation of the epigenetic status of the fungal cells by the introduction of an epigenetic modifier into the fungal can induce a change in the gene expression within the fungal cells. This can induce the fungal cells in culture to produce compounds not normally or naturally manufactured by fungal cells.

After epigenetic modification, compounds can be extracted and/or partitioned from the fungal cells and/or culture media. Suitable extraction and partitioning techniques are generally known in the art. The compounds can be purified using purification techniques generally known in the art, including but not limited to various chromatography techniques (e.g. various liquid chromatography techniques). The compounds can be analyzed and characterized using a suitable technique such as nuclear magnetic resonance (NMR) and mass spectroscopy. Other suitable techniques will be appreciated by those of ordinary skill in the art in view of this description. The produced and extracted compounds can be assayed for bioactivity, antibacterial, antiparasitic, antifungal, antiviral, and other attributes using a suitable assay technique generally known in the art.

As such, the methods of epigenetically modifying fungal cells can be used to produce non-natural compounds that are not found un-modified fungal cells. Furthermore, these compounds can be purified or otherwise isolated or concentrated.

In certain embodiments of the present disclosure, compositions as described herein can consist of or consist essentially of Compound 1. In certain embodiments of the present disclosure, pharmaceutical compositions as described herein can consist or consist essentially of Compound 1 (in an effective amount, or a dose that can provide an effective amount) and a pharmaceutically acceptable carrier.

Fungal Culture

Fungi as described herein can be cultured according to the following variables:
  M—Media: rice (R), action agar glycerol (A), potato dextrose+agar (B), Sabaurough dextrose broth+agar (C), malt broth+agar (D)
  T—Temperature (23° C., 30° C.)
  X—Light (exposed to light (L), dark (D))
  Z—Amount of fungus inoculated (2, 4 or 8 pieces)
  Y—pH (acidic, basic) or Salinity (0.34%, 0.68%)
  E—Cultivation period (7 days (E1), 14 days (E2))

M-T-X-Y-Z-E                    Fraction Name ID/Formula:

The culturing can be performed with a media. In embodiments according to the present disclosure, the media is selected from the group consisting of: rice, action agar glycerol, potato dextrose and agar, Sabaurough dextrose broth and agar, and malt broth and agar. As the skilled artisan would understand, these media are commercially available, and can be prepared according to methods as known in the art, including the recommendations of the manufacturer.

The culturing can be performed at a temperature. In embodiments according to the present disclosure, the temperature can be about 20° C. to about 40° C. in embodiments according to the present disclosure, the temperature can be about 23° C. or about 30° C.

The culturing can be performed in light or dark, wherein the culture conditions are continuously light or continuously dark.

The culturing can be performed with an amount of fungus inoculated. In embodiments according to the present disclosure, the amount of fungus can be about 1 to about 10 pieces.

In embodiments according to the present disclosure, the amount of fungus inoculated can be 2 pieces, 4 pieces, or 8 pieces.

The culturing can be performed at acidic or basic pH. In embodiments according to the present disclosure, an acidic pH is a pH of <7, a basic pH has pH>7. In embodiments according to the present disclosure, an acidic pH is about 6.2 and a basic (i.e. alkaline) pH is about 8.3.

The culturing can be performed at a saline percent. In embodiments according to the present disclosure, the saline percent (i.e. salinity) can be about 0.0001% to about 1%. In embodiments according to the present disclosure, the saline percent (i.e. salinity) can be about 0.34% or about 0.68%.

The culturing can be performed for a cultivation period. In embodiments according to the present disclosure, the cultivation period can be about 7 days to about 40 days. In embodiments according to the present disclosure, the cultivation period can be 7 days or 14 days, or about 7 days to about 14 days.

In an embodiment according to the present disclosure, the culture conditions can be of the fraction ID name or formula D-23-L-2-ba-E1. This corresponds to the culture conditions of malt broth+agar media, 23° C. incubation temperature, light, 2 pieces of fungus inoculated, basic pH, and a cultivation period of 7 days. The salinity for this embodiment can be about 0.34%.

In an embodiment according to the present disclosure, the culture conditions can be of the fraction ID name or formula B-30-D-2-ac-E2. This corresponds to the culture conditions of potato dextrose+agar media, 30° C. incubation temperature, dark, 2 pieces of fungus inoculated, acidic pH, and a cultivation period of 14 days. The salinity for this embodiment can be about 0.34%.

Additional embodiments of combinations of culture conditions according to the present disclosure and formula ID above are as follows: A-23-L-8-ac-E2; R-23-L-8-0.68-E1; A-23-L-4-ba-E1; R-23-L-2-0.68-E1; R-23-L-4-0.68-E2; R-23-L-4-ba-E2; R-23-L-4-ba-E1; R-23-L-8-ba-E1; R-23-L-2-0.34-E1; R-23-L-2-0.34-E2; R-23-L-8-0.34-E1; A-23-L-4-ac-E1; C-23-L-8-ba-E1; D-23-L-2-ba-E1; D-23-L-4-ba-E1; R-23-L-4-ac-E1; R-23-L-8-0.34-E2; A-23-L-2-ac-E1; B-23-L-2-E1; D-23-L-2-ac-E1; A-23-L-2-0.34-E1; A-23-L-2-0.34-E2; A-23-L-2-E1; A-23-L-4-ba-E2; B-23-L-2-ba-E1; B-23-D-2-ba-E1; C-23-L-8-ac-E2; D-23-L-2-ba-E2; D-23-L-4-0.34-E1; D-23-L-4-ac-E2; A-30-L-2-E1; R-30-L-2-0.34-E2; R-30-L-8-0.34-E1; B-23-L-8-ba-E1; B-23-L-4-0.34-E2; B-30-L-2-ac-E1; C-23-L-2-ac-E1; C-23-L-2-ac-E2; A-30-L-2-ac-E1; R-30-L-4-0.34-E2; A-30-D-8-0.34-E1; A-30-L-8-ac-E1; A-30-L-8-ac-E2; B-30-L-2-E2; B-30-L-8-ac-E2; C-30-L-2-E1; C-30-L-2-E2; C-30-L-4-ac-E1; D-23-L-4-ac-E1; R-30-L-4-0.68-E1; B-23-D-4-ba-E2; R-30-L-2-0.34-E1; B-23-L-8-0.34-E2; C-30-L-4-ac-E2; C-30-L-8-ac-E1; C-30-L-8-ac-E2; R-30-L-4-0.68-E2; R-30-L-2-E1; C-30-L-2-ac-E1; and C-30-L-8-ba-E1.

These combinations correspond to (respectively):
action agar glycerol, 23° C., light, 8 pieces inoculated, acidic pH, 14 day cultivation period;
rice, 23° C., light, 8 pieces inoculated, 0.68% salinity, 7 day cultivation period;
action agar glycerol, 23° C., light, 4 pieces inoculated, basic pH, 14 day cultivation period;
rice, 23° C., light, 2 pieces inoculated, 0.68% salinity, 7 day cultivation period;
rice, 23° C., light, 4 pieces inoculated, 0.68% salinity, 14 day cultivation period;
rice, 23° C., light, 4 pieces inoculated, basic pH, 14 day cultivation period;
rice, 23° C., light, 4 pieces inoculated, basic pH, 7 day cultivation period;
rice, 23° C., light, 8 pieces inoculated, basic pH, 7 day cultivation period;
rice, 23° C., light, 2 pieces inoculated, 0.34% salinity, 7 day cultivation period;
rice, 23° C., light, 2 pieces inoculated, 0.34% salinity, 14 day cultivation period;
rice, 23° C., light, 8 pieces inoculated, 0.34% salinity, 7 day cultivation period;
action agar glycerol, 23° C., light, 4 pieces inoculated, acidic pH, 7 day cultivation period;
dextrose broth+agar, 23° C., light, 8 pieces inoculated, 7 day cultivation period;
malt broth+agar, 23° C., light, 2 pieces inoculated, basic pH, 7 day cultivation period;
malt broth+agar, 23° C., light, 4 pieces inoculated, basic pH, 7 day cultivation period;
rice, 23° C., light, 4 pieces inoculated, basic pH, 7 day cultivation period;
rice, 23° C., light, 8 pieces inoculated, 0.34% salinity, 14 day inoculation period;
action agar glycerol, 23° C., light, 2 pieces inoculated, acidic pH, 7 day cultivation period;
potato dextrose+agar, 23° C., light, 2 pieces inoculated, 7 day cultivation period;
malt broth+agar, 23° C., light, 2 pieces inoculated, acidic pH, 7 day cultivation period;
action agar glycerol, 23° C., light, 2 pieces inoculated, 0.34% salinity, 14 day cultivation period;
action agar glycerol, 23° C., light, 2 pieces inoculated, 0.34% salinity, 7 day cultivation period;
action agar glycerol, 23° C., light, 2 pieces inoculated, 7 day cultivation period;
action agar glycerol, 23° C., light, 4 pieces inoculated, basic pH, 14 day cultivation period;
potato dextrose+agar, 23° C., light, 2 pieces inoculated, basic pH, 7 day cultivation period;
potato dextrose+agar, 23° C., dark, 2 pieces inoculated, basic pH, 7 day cultivation period;
dextrose broth+agar, 23° C., light, 8 pieces inoculated, acidic pH, 7 day cultivation period;
malt broth+agar, 23° C., light, 2 pieces inoculated, basic pH, 14 day cultivation period;
malt broth+agar, 23° C., light, 4 pieces inoculated, 0.34% salinity, 7 day cultivation period;
malt broth+agar, 23° C., light, 4 pieces inoculated, acidic pH, 14 day cultivation period;
action agar glycerol, 30° C., light, 2 pieces inoculated, 7 day cultivation period;
rice, 30° C., light, 2 pieces inoculated, 0.34% salinity, 14 day inoculation period;
rice, 30° C., light, 8 pieces inoculated, 0.34% salinity, 7 day inoculation period;
potato dextrose+agar, 23° C., light, 8 pieces inoculated, basic pH, 7 day cultivation period;
potato dextrose+agar, 23° C., light, 4 pieces inoculated, 0.34% salinity, 14 day cultivation period;
potato dextrose+agar, 30° C., light, 2 pieces inoculated, acidic pH, 7 day cultivation period;
dextrose broth+agar, 23° C., light, 2 pieces inoculated, acidic pH, 7 day cultivation period;
dextrose broth+agar, 23° C., light, 2 pieces inoculated, acidic pH, 14 day cultivation period;
action agar glycerol, 30° C., light, 2 pieces inoculated, acidic pH, 7 day cultivation period;

rice, 30° C., light, 4 pieces inoculated, 0.34% salinity, 14 day cultivation period;
action agar glycerol, 30° C., dark, 8 pieces inoculated, 0.34% salinity, 7 day cultivation period;
action agar glycerol, 30° C., light, 8 pieces inoculated, acidic pH, 7 day cultivation period;
action agar glycerol, 30° C., light, 8 pieces inoculated, acidic pH, 14 day cultivation period;
potato dextrose+agar, 30° C., light, 2 pieces inoculated, 14 day cultivation period;
potato dextrose+agar, 30° C., light, 2 pieces inoculated, acidic pH, 14 day cultivation period;
dextrose broth+agar, 30° C., light, 2 pieces inoculated, 7 day cultivation period;
dextrose broth+agar, 30° C., light, 2 pieces inoculated, 14 day cultivation period;
dextrose broth+agar, 30° C., light, 4 pieces inoculated, acidic pH, 7 day cultivation period;
malt broth+agar, 23° C., light, 4 pieces inoculated, acidic pH, 7 day cultivation period;
rice, 30° C., light, 4 pieces inoculated, 0.68% salinity, 7 day cultivation period;
potato dextrose+agar, 23° C., dark, 4 pieces inoculated, basic pH, 14 day cultivation period;
rice, 30° C., light, 2 pieces inoculated, 0.34% salinity, 7 day cultivation period;
rice, 23° C., light, 8 pieces inoculated, 0.34% salinity, 14 day cultivation period;
dextrose broth+agar, 30° C., light, 4 pieces inoculated, acidic pH, 7 day cultivation period;
dextrose broth+agar, 30° C., light, 8 pieces inoculated, acidic pH, 7 day cultivation period;
dextrose broth+agar, 30° C., light, 8 pieces inoculated, acidic pH, 14 day cultivation period;
rice, 30° C., light, 4 pieces inoculated, 0.68% salinity, 14 day cultivation period;
rice, 30° C., light, 2 pieces inoculated, 7 day cultivation period;
dextrose broth+agar, 30° C., light, 2 pieces inoculated, acidic pH, 7 day cultivation period; and
dextrose broth+agar, 30° C., light, 8 pieces inoculated, basic pH, 7 day cultivation period.

In certain aspects, the methods and fungal culture conditions described above are culture conditions suitable for the production of Compound 1, below.

In certain aspects, the methods of fungal culture as described herein are methods of fungal culture of an endophytic fungus of the La Encrucijada tropical mangrove of Tapachula (Chiapas, Mexico) that are suitable to produce Compound 1, below.

Antileishmanial Compounds and Formulations Thereof

Leishmaniasis is a parasitic disease caused by infection with *Leishmania* parasites, which can be spread by the bite of infected sand flies. The most common forms in humans are cutaneous leishmaniasis and visceral leishmaniasis. Up to 12 million people are estimated to be infected, a number that increases by 2 million annually. Described herein are compounds and formulations thereof that can kill and/or inhibit leishmanial parasites. Parasite inhibition can comprise inhibition of parasitic development, inhibition of parasitic spreading, inhibition of parasitic reproduction, inhibition of parasitic proliferation, or the like. In some embodiments, the compound can be compound (1). Compound (1) can be effective to kill and/or inhibit leishmanial parasites.

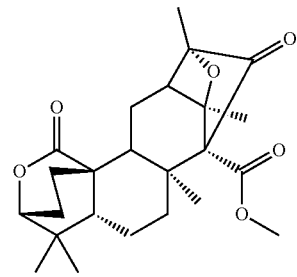

(1)

Compound (1) can be produced by culturing an endophytic fungus from a mangrove plant in the presence of an HDAC inhibitor (e.g. sodium butyrate) and/or a DNMT inhibitor (e.g. 5-azacytidine). After production, the compound according to Formula (1) can be extracted and purified according to techniques generally known in the art.

Formulations Containing Compound (1)

Compound (1) can be included in a formulation, formulation that, in addition to the compound, can further include a suitable carrier. The carrier can be a pharmaceutically acceptable carrier. The formulation can be a pharmaceutical formulation. The compounds and/or formulations thereof described herein can be administered to a subject. The subject can be infected with or be suspected of being infected with a leishmanial parasite. The subject can be a subject in need thereof. The compounds and formulations described herein can be administered by a suitable route, such as but not limited to oral, infusion, and intravenous. Other suitable routes are described elsewhere herein.

Parenteral Formulations

Compound (1) and formulations thereof described herein can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the Compound (1) and formulations thereof described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of Compound (1).

The formulation can be buffered to a pH of 3-8 for parenteral administration upon reconstitution. In some aspects, the pH of the formulation can be a pH of about 7.0-7.4 upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating Compound (1) in the desired amount in the appropriate solvent or dispersion medium with one or more of the excipients listed above, as required, followed by filtered sterilization. Dispersions can be prepared by incorporating the Compound (1) into a sterile vehicle which contains the basic dispersion medium and the required other ingredients from those listed above. Sterile powders for the preparation of sterile injectable solutions can be prepared by vacuum-drying and freeze-drying techniques, which yields a powder of the Compound (1) with or without any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of Compound (1). Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, and use of nanotechnology including nanoformulations for parenteral administration can also contain one or more excipients, such as dispersing agents, wetting agents, and suspending agents.

Topical Formulations

Compound (1) can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, Compound (1) can be administered as a liquid formulation, such as a solution or suspension, a semi-solid formulation, such as a lotion or ointment, or a solid formulation. In some embodiments, Compound (1) can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing Compound (1) are also described herein. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing Compound (1) are also described herein. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing Compound (1) and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing Compound (1), a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alkylene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include Compound (1). Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

Compound (1) can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing Compound (1) can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing Compound (1) can be prepared using one or more pharmaceutically acceptable excipients, including diluents, preservatives, binders, lubricants, disintegrators, swelling agents, fillers, stabilizers, and combinations thereof.

Delayed release dosage formulations containing Compound (1) can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing Compound (1) can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, days, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Methods of Treating Leishmaniosis

In use, Compound (1) and formulations thereof described herein can be administered to a subject. In some embodiments, the subject is infected with or is suspected of being infected with a leishmanial parasite. Compound (1) or formulation thereof described herein can be co-administered or be a co-therapy with another active agent or ingredient that can be included in the formulation or provided in a dosage form separate from the Compound (1) or formulation thereof.

The amount of Compound (1) or formulation thereof can range from about 0.01 μg/kg to up to about 1000 mg/kg or more, depending on the factors mentioned elsewhere herein. In certain embodiments, the amount can range from 0.01 μg/kg up to about 500 mg/kg, or 1 μg/kg up to about 500 mg/kg, 5 μg/kg up to about 500 mg/kg, 0.01 μg/kg up to about 100 mg/kg, or 1 μg/kg up to about 100 mg/kg, 5 μg/kg up to about 100 mg/kg.

Administration of Compound (1) or formulation thereof can be systemic or localized. The Compound (1) or formulation thereof can be administered to the subject in need thereof one or more times per hour or day. In embodiments, the Compound (1) or formulation thereof can be administered once daily. In other embodiments, Compound (1) or formulation thereof can be administered can be administered 2, 3, 4, 5, 6, 7, 8, 9, 10, 11, 12, or more times daily. In some embodiments, when administered, an effective amount of Compound (1) or formulation thereof can be administered to the subject in need thereof. Compound (1) or formulation thereof can be administered one or more times per week. In some embodiments, Compound (1) or formulation thereof can be administered 1, 2, 3, 4, 5, 6 or 7 days per week. In some embodiments, Compound (1) or formulation thereof can be administered 1, 2, 3, 4, 5, 6, 7, 8, 9, 10, 11, 12, or more times per month. In some embodiments, Compound (1) or formulation thereof can be administered 1, 2, 3, 4, 5, 6, 7, 8, 9, 10, 11, 12, 13, 14, 15, 16, 17, 18, or more time per year.

In some embodiments, Compound (1) or formulation thereof can be administered in a dosage form. The amount or effective amount of Compound (1) or formulation thereof can be divided into multiple dosage forms. For example, the effective amount can be split into two dosage forms and the one dosage forms can be administered, for example, in the morning, and the second dosage form can be administered in the evening. Although the effective amount can be given over two or more doses, in one day, the subject can receives the effective amount when the total amount administered across all the doses is considered. The dosages can range from about 0.01 μg/kg to up to about 1000 mg/kg or more, depending on the factors mentioned above. In certain embodiments, the dosage can range from 0.01 μg/kg up to about 500 mg/kg, or 1 μg/kg up to about 500 mg/kg, 5 μg/kg up to about 500 mg/kg, 0.01 μg/kg up to about 100 mg/kg, or 1 μg/kg up to about 100 mg/kg, 5 μg/kg up to about 100 mg/kg.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Endophytic fungus was obtained from tropical mangrove. The fungus was grown/maintained in culture for a period of time and exposed to an amount of one or more epigenetic modifiers (e.g. sodium butyrate and/or 5-azacytidine) to modify the endophytic fungus. A sample of the endophytic fungus was deposited at the American Type Culture Collection (ATCC) Patent Depository, 10801 University Blvd. Manassas, Virginia, 20110-2209 USA, on Mar. 20, 2024, under accession number PTA-127738, pursuant to the Budapest Treaty on the International Recognition of the Deposit of Microorganisms for the Purposes of Patent Procedure. After exposure, compounds were extracted from the fungus and/or culture media, partitioned, purified, and characterized using various extraction, partitioning, and purification techniques generally known in the art. Purification and characterization was carried out, for example, using a liquid chromatography technique (such as MPLC and/or HPLC), spectrometric techniques (e.g. mass spectrometry and/or NMR), and various bioassays to determine, inter alia, the anti-infective, and/or anti-parasitic properties. See e.g. FIG. 1.

Figure 5:
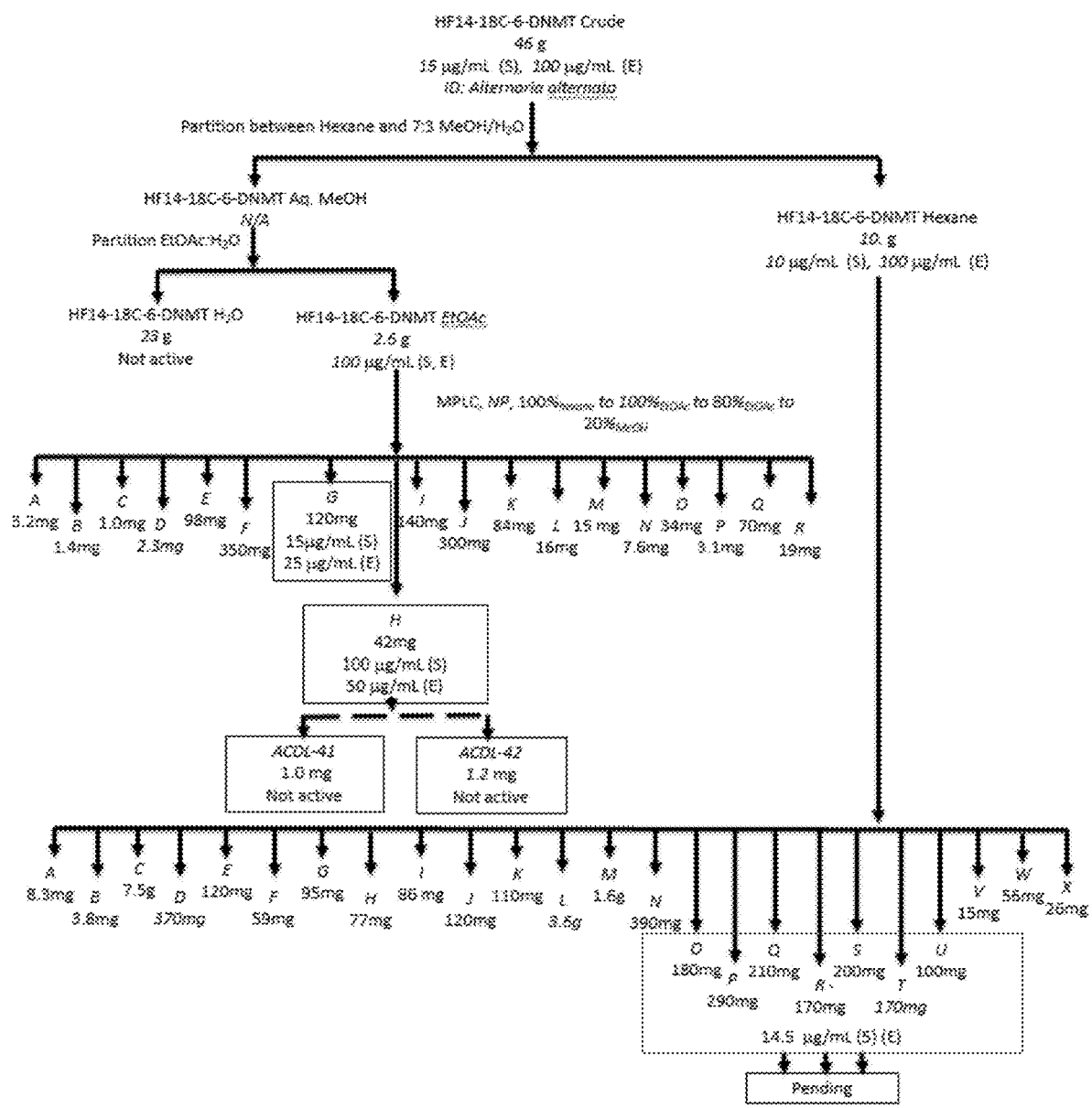
FIG. 5 shows a partitioning scheme to obtain antibacterial compounds produced in epigenetically modified mangrove cells.
Figure 6A:
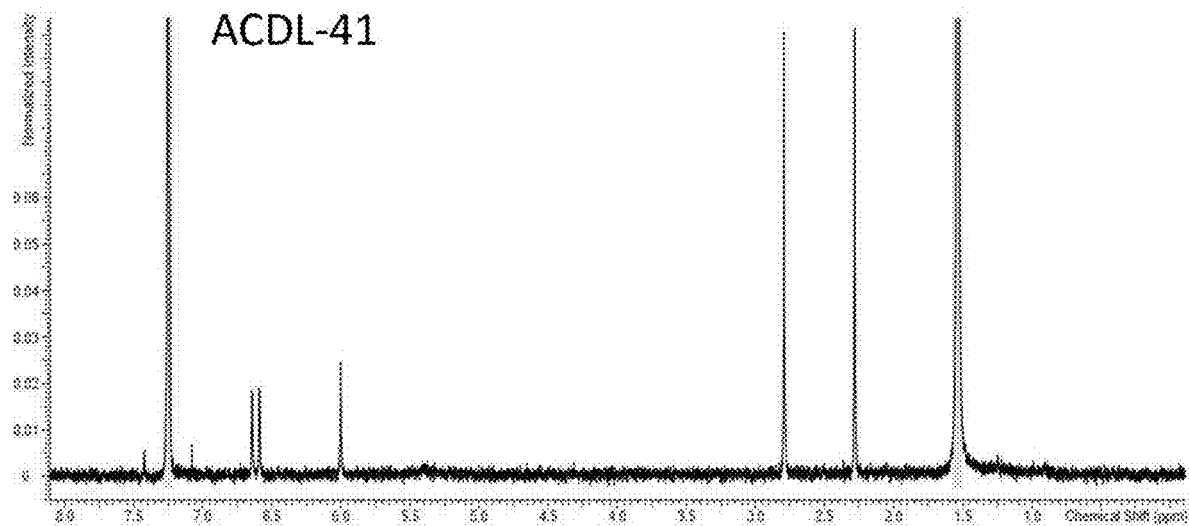
FIGS. 6A-6B shows NMR analysis results from potential antibacterial compounds partitioned according to the scheme in FIG. 5.
Figure 6B:
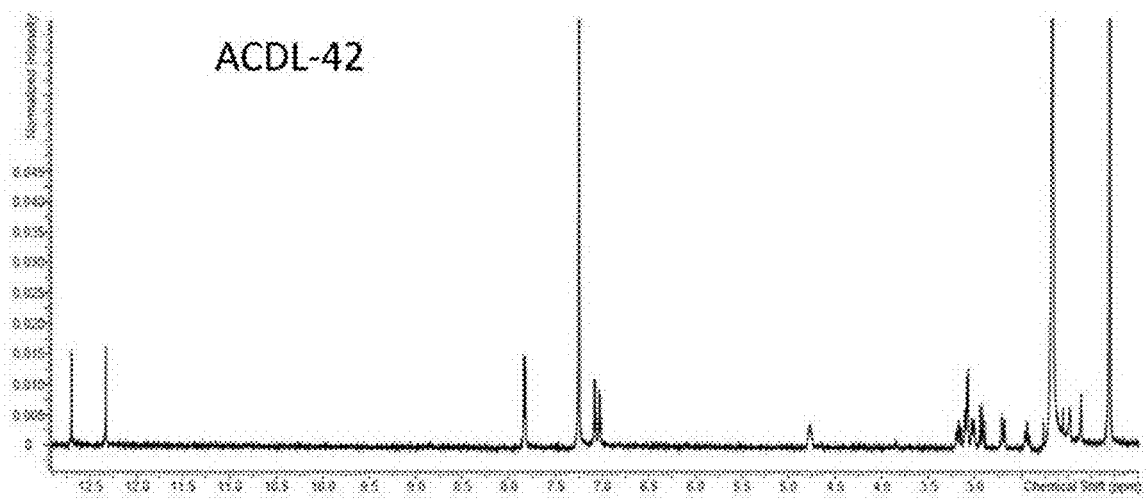

Compounds were generated that were screed for antileishmanial activity. Results are shown in FIGS. 2, FIGS. 3A-3D, and FIGS. 4A-4C. Compound ACDL-34 (referred to as Compound (1) elsewhere herein) was observed to have antileishmanial activity. See e.g. FIGS. 4A-4C. Other compounds having potential antibacterial activity were also produced. See e.g. FIG. 5 and FIGS. 6A-6B.

Example 2

Microorganisms, specifically fungi, have a significant ability to produce bioactive metabolites that can be used in the discovery and development of pharmaceuticals. Epigenetic regulation is a key mechanism to orchestrate the expression or suppression of gene activity in laboratory conditions; hence, manipulating these mechanisms offers new opportunities to express down-regulated secondary metabolite genes and has the potential to generate new potent and novel metabolites.

Although it is possible to mimic the fungi's natural environment, more evidence correlating specific biological variables with fungal growth is needed in order to optimize the culture's metabolite production yields. To identify a correlation between culture conditions and production yields, the fungus of interest was grown on five different media, each exposed to six variables: temperature, light, amount of fungus initially inoculated, pH, salinity and cultivation period.

The extraction with ethyl acetate of 520 individual cultivation conditions led to crude extracts. These crude extracts were filtered, then analyzed with coupled Liquid Chromatography-Mass Spectroscopy (LC-MS/MS) technique. The previous chemical investigation of an unidentified fungal endophyte from La Encrucijada tropical mangrove of Tapachula (Chiapas, Mexico), treated with epigenetic DNA Methyl Transferase Inhibitor (DNMTi) revealed the presence of a novel sesterterpene active against the *Leishmania donovani* parasite. The data analysis describes which major variable or combination of variables can be optimal for production of the compound of interest.

Figure 4B:
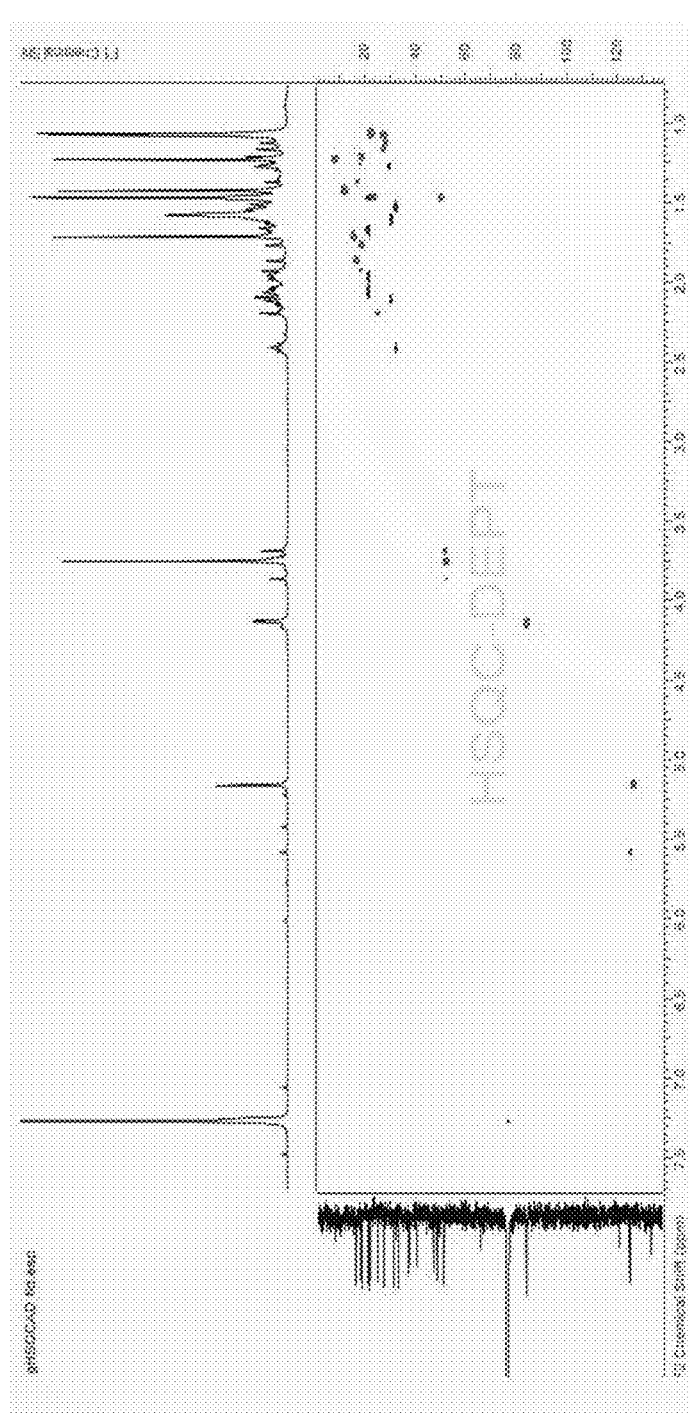
Figure 4C:
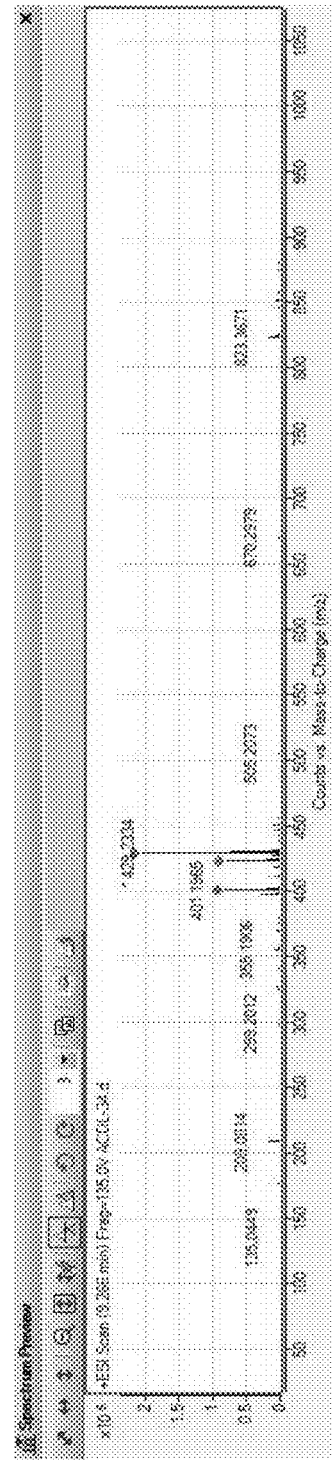

FIGS. 4A-4C show the structure, characterization, and bioactivity of a targeted antileishmanaial sesterterpene (ACDL-34).

Figure 7:
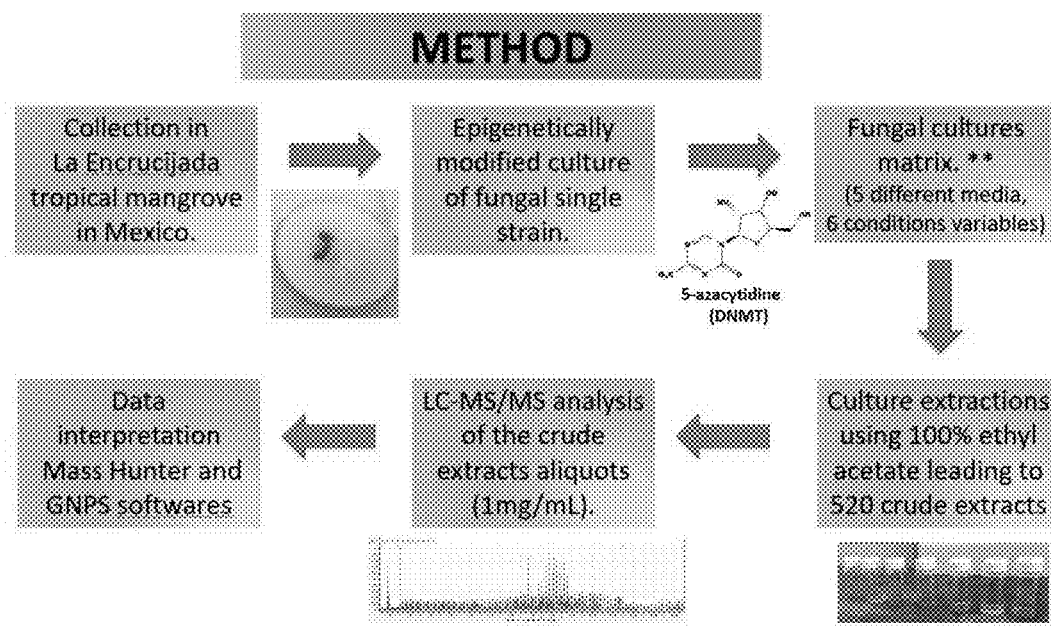
FIG. 7 is a flowchart depicting an embodiment of a method according to the present disclosure.

FIG. 7 is a flowchart of an embodiment of a method according to the present disclosure. A fungal culture matrix was establishing using the following culture conditions:

M—Media: rice (R), action agar glycerol (A), potato dextrose+agar (B), Sabaurough dextrose broth+agar (C), malt broth+agar (D)

T—Temperature (23° C., 30° C.)

X—Light (exposed to light (L), dark (D))

Z—Amount of fungus inoculated (2, 4 or 8 pieces)

Y—pH (acidic, basic) or Salinity (0.34%, 0.68%)

E—Cultivation period (7 days (E1), 14 days (E2))

Figure 8A:
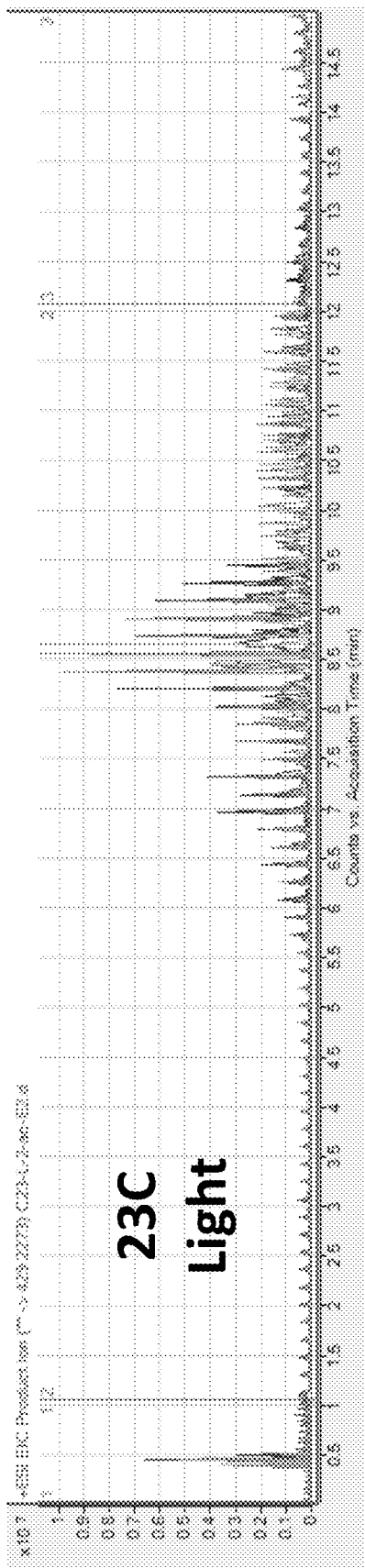
FIGS. 8A-8D are superimposed chromatograms of crude extracts according to light and temperature variables.
Figure 8B:
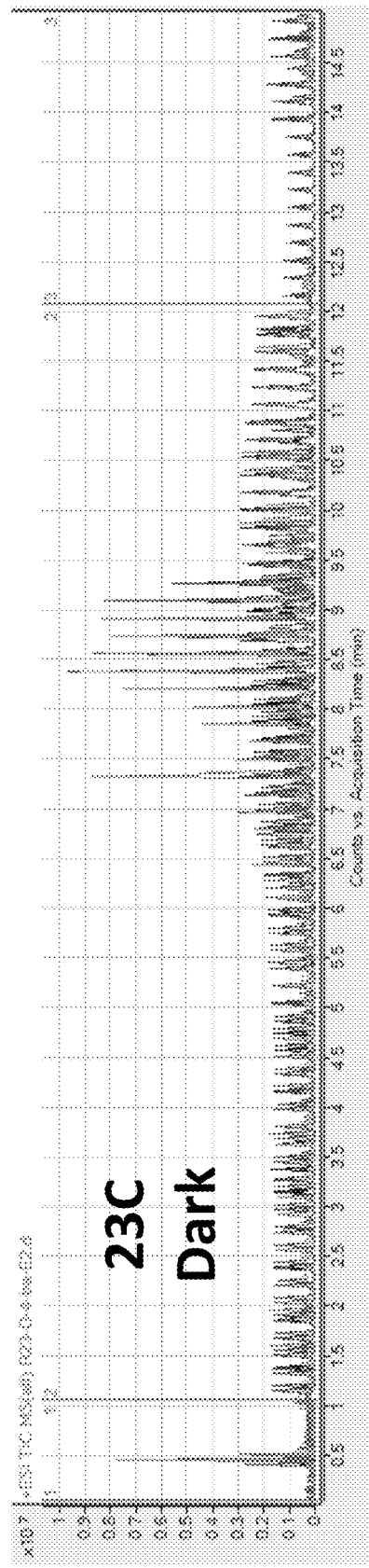
Figure 8C:
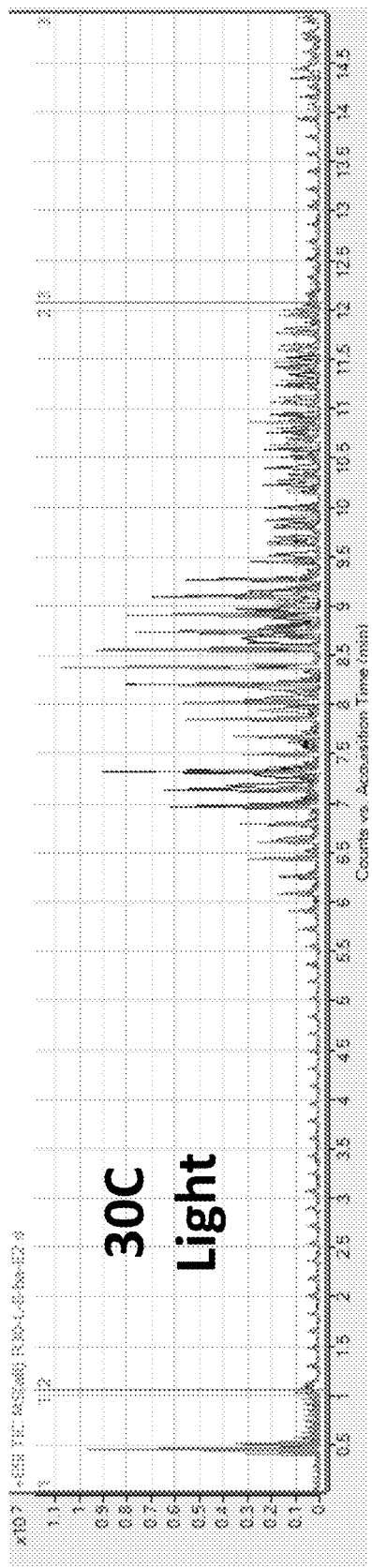
Figure 8D:
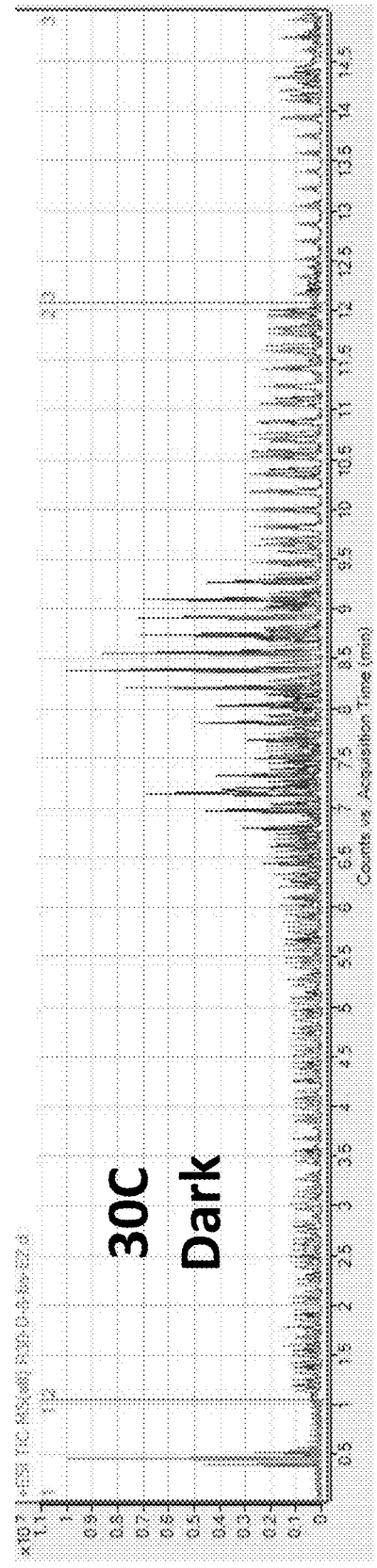

M-T-X-Y-Z-E                     Fraction Name ID:

Following methods of the present disclosure, LC MS-MS analysis was performed, and 520 extracts were screened for the mass 429.2313 g/mol of ACDL-34 (accuracy error of $-2.7 \times 10^{-14}$ ppm). FIGS. 8A-8D are superimposed chromatograms of crude extracts according to light and temperature variables. FIGS. 8A-8B are results at 23° C. with light (FIG. 8A) and dark (FIG. 8B), and FIGS. 8C-8D are results at 30° C. with light (FIG. 8C) and dark (FIG. 8D).

Figure 9A:
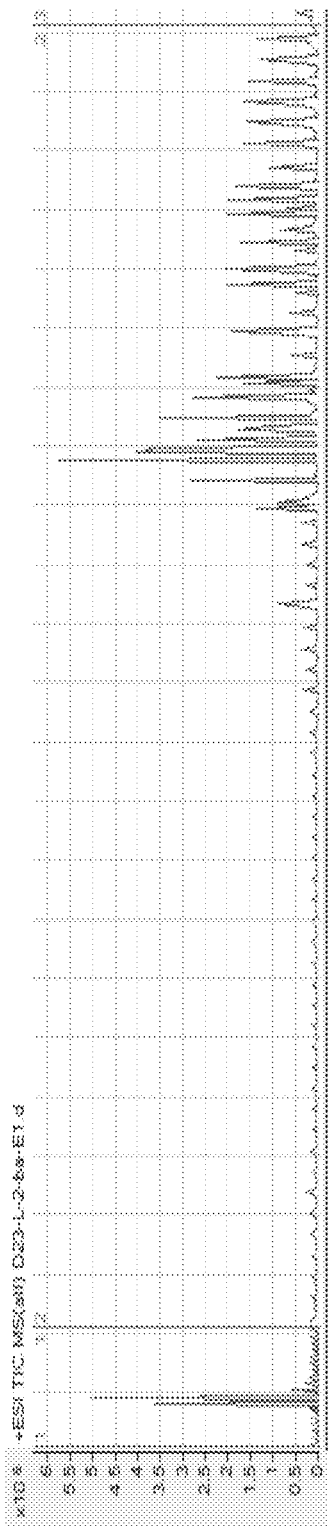
FIGS. 9A-9C show comparisons of LC MS MS data for both best cultures found.
Figure 9B:
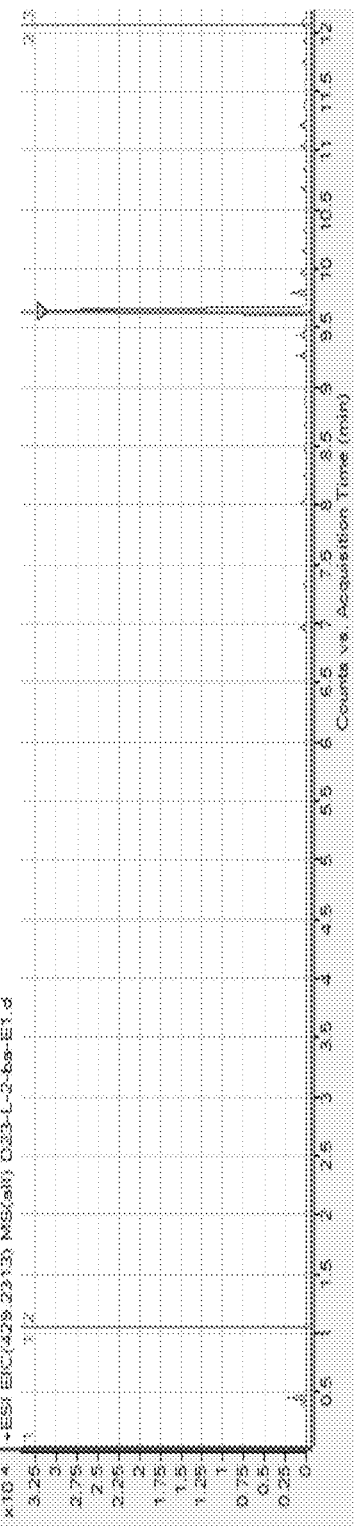
Figure 9C:
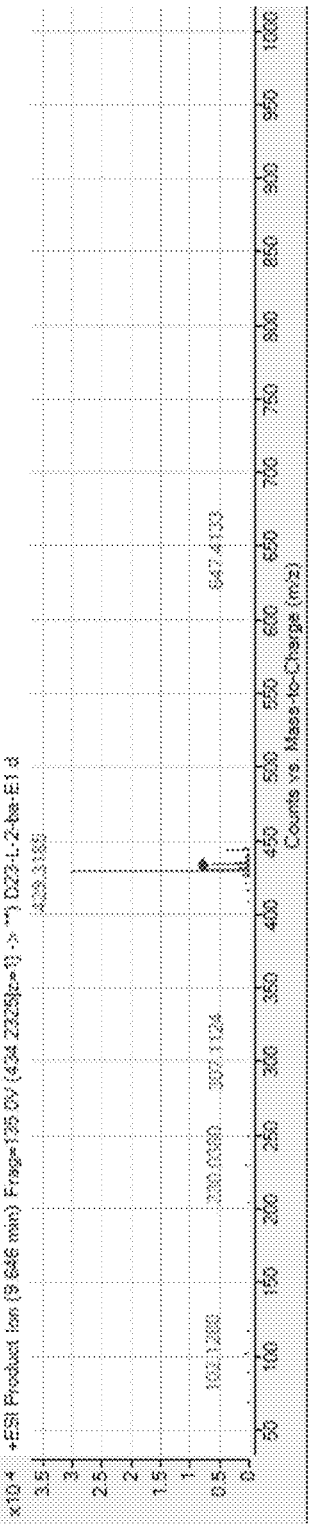

FIGS. 9A-9C show comparisons of LC MS MS data for both best cultures found.

FIGS. 10A-10C are a continuation of the LC MS MS data of FIGS. 9A-9C for both best cultures found.

Figure 11:
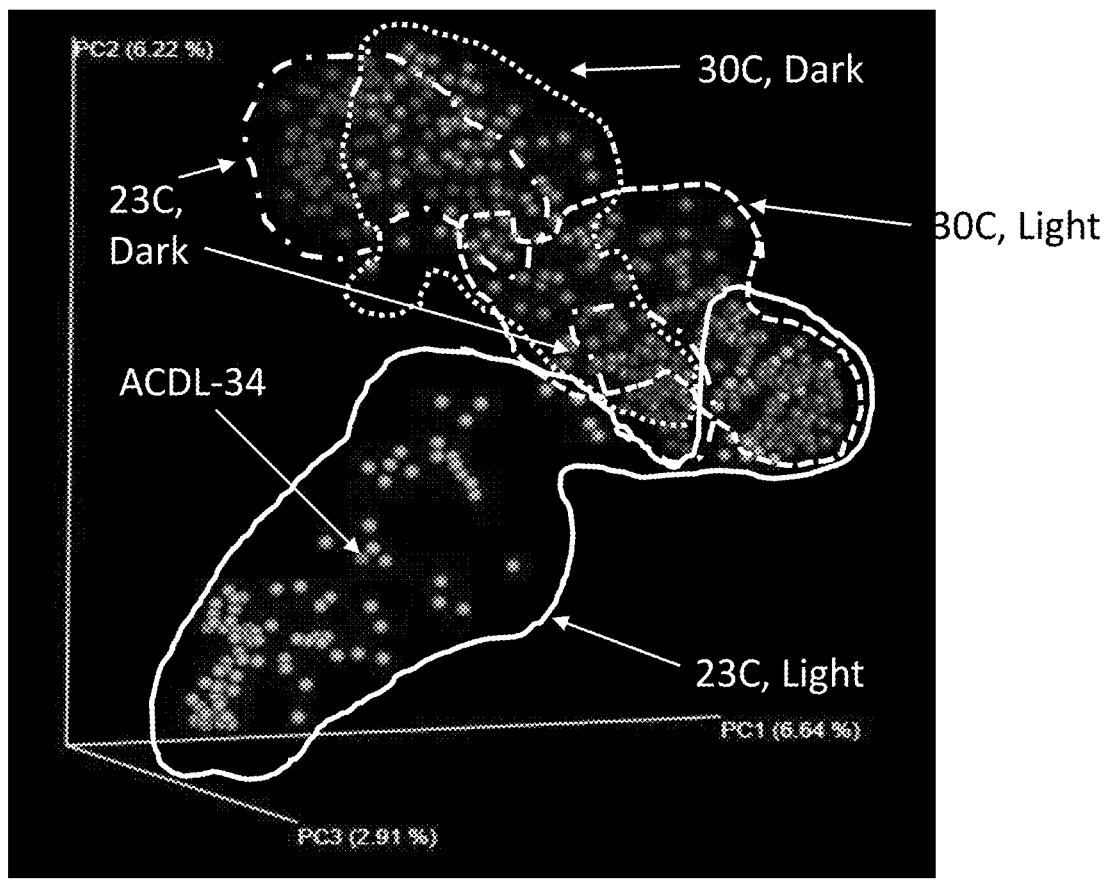
FIG. 11 is a principal component plot of a Global Natural Products Social Networking (GNPS) analysis describing the resemblance between the screened crude extracts and ACDL-34. PC1 is the cosine value, PC2 the peak intensity from mass spectrum (MS), and PC3 is the Jacquard distance.

FIG. 11 is a principal component plot of a Global Natural Products Social Networking (GNPS) analysis describing the resemblance between the screened crude extracts and ACDL-34. PC1 is the cosine value, PC2 the peak intensity from mass spectrum (MS), and PC3 is the Jacquard distance.

From the LC MS-MS data, a suitable culture (more suitable than others) was found yielding a compound matching the mass of ACDL-34: D-23-L-2-ba-E1. This corresponds to the culture conditions of malt broth+agar media, 23° C. incubation temperature, light, 2 pieces of fungus inoculated, basic pH, and a cultivation period of 7 days.

From the GPNS analysis, a suitable culture (more suitable than others) was found yielding a compound matching the mass of ACDL-34: B-30-D-2-ac-E2. This corresponds to the culture conditions of potato dextrose+agar media, 30° C. incubation temperature, dark, 2 pieces of fungus inoculated, acidic pH, and a cultivation period of 14 days.

Out of 520 cultures, the presence of ACDL-34 was detected in 130 cultures. Significant factors affecting production of ACDL-34 by epigenetically modified fungus appeared to be light, temperature, pH, and salinity.

Figure 12A:
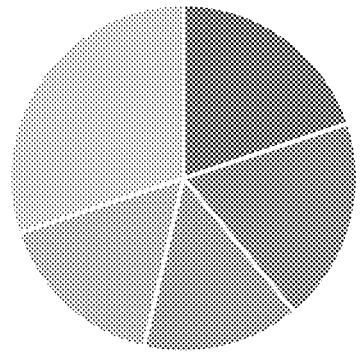
FIGS. 12A-12E illustrate the overall distribution of ACDL-34 based on culture conditions.
Figure 12B:
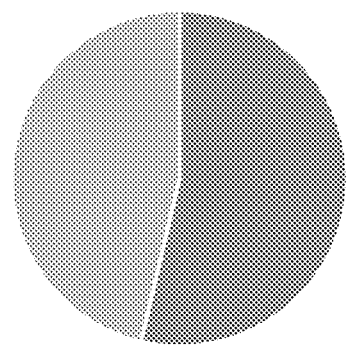
Figure 12C:
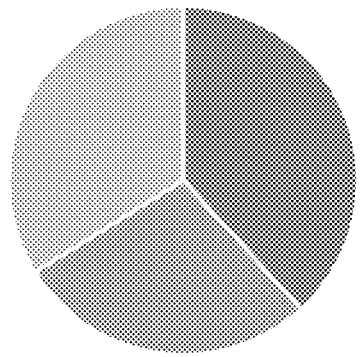
Figure 12D:
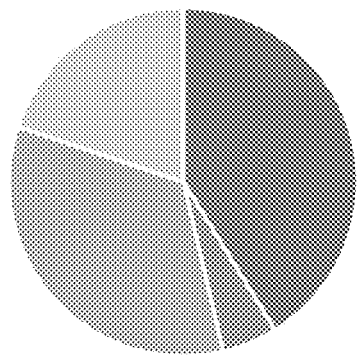
Figure 12E:
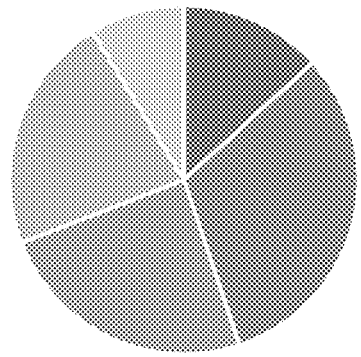

FIGS. 12A-12E illustrate the overall distribution of ACDL-34 based on culture conditions. Each pie chart illustrates a comparison of culture conditions that resulted in the production of ACDL-34 from the total of 520 tested. FIG. 12A shows the presence of ACDL-34 as a function of culture media. FIG. 12B shows the presence of ACDL-34 based on extraction time. FIG. 12C shows the presence of ACDL-34 based on the amount of inoculated fungus. FIG. 12D shows the presence of ACDL-34 based on light and temperature variations. FIG. 12E shows the presence of ACDL-34 based on medium modification.

Figure 13A:
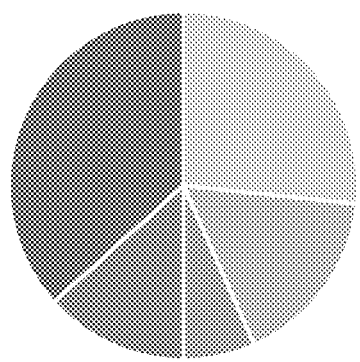
FIGS. 13A-13E illustrate the distribution of ACDL-34 within TOP 30 culture conditions.
Figure 13B:
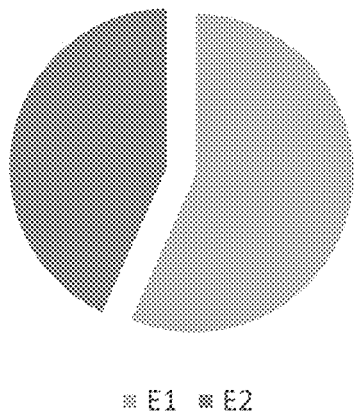
Figure 13C:
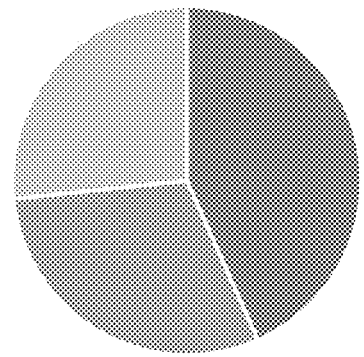
Figure 13D:
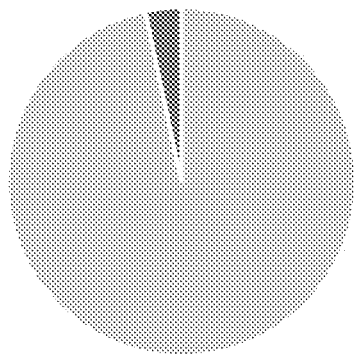
Figure 13E:
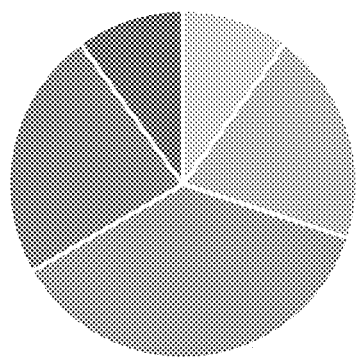

FIGS. 13A-13E illustrate the distribution of ACDL-34 within TOP 30 culture conditions. FIG. 13A shows the top 30 cultures of the total that were investigated producing ACDL-34 based on media distribution. FIG. 13B shows the top 30 cultures producing ACDL-34 based on extraction time. FIG. 13C shows the top 30 cultures producing ACDL-34 based on amount of inoculated fungus. FIG. 13D shows the top 30 cultures producing ACDL-34 based on light and temperature variations. FIG. 13E shows the top 30 cultures producing ACDL-34 based on medium modifications.

The metabolomic analysis revealed conditions which can bring forward the targeted compound ACDL-34. Production of the potential ACDL-34 metabolite is possible with the various media conditions tested; however, the process was most successful with media B and D. There is evidence suggesting that pH conditions are the most affecting variable in the growth of this particular fungal strain coupled with production of ACDL-34. Additionally, an antagonistic light/temperature relationship seems essential for successful growth and metabolite production.

Using the conditions describing the cultures B-30-D-2-ac and D-23-L-2-ba the fungus culture can be scaled up on a scale of up to 100 times larger. A targeted LC-MS/MS approach can guide the fractionation of the two crude extracts obtained and the chromatographic isolation and purification of more ACDL-34 compound of interest.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

At least the following is claimed:

1. A composition comprising Compound (1)

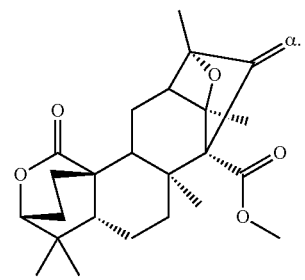

(1)

2. The composition of claim 1, wherein the composition comprises an amount of Compound 1 effective to kill and/or inhibit a leishmanial parasite.

3. A pharmaceutical formulation comprising:

an amount of Compound (1)

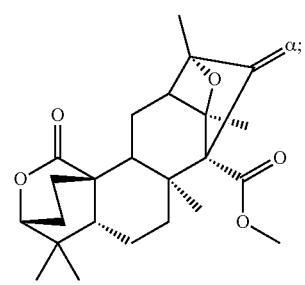

(1)

and a pharmaceutically acceptable carrier.

4. The pharmaceutical formulation of claim 3, wherein the amount is an effective amount sufficient to kill a leishmanial parasite, inhibit a leishmanial parasite, or both.

5. The pharmaceutical formulation of claim 3, wherein the amount of Compound (1) is from about 0.01 µg to about 1000 mg or more.

\* \* \* \* \*